United States Patent [19]

Garabedian

[11] Patent Number: Plant 5,904

[45] Date of Patent: Mar. 17, 1987

[54] PLUM TREE "SANTA ROSA-TWO"

[76] Inventor: John M. Garabedian, 3104 E. Huntington Blvd., Fresno, Calif. 93702

[21] Appl. No.: 766,447

[22] Filed: Aug. 19, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Santa Rosa Plum Tree (unpatented), with which it is most similarly related, and which is characterized by fruit which is deeper and fuller in external color, larger in size, and possesses an Amber-colored flesh which is lightly streaked in Red near the cavity of the fruit.

1 Drawing Figure

BACKGROUND OF THE NEW VARIETY

The present invention relates to a plum tree, known as the "Santa Rosa-Two", and more particularly to such a plum tree which bears large, uniform, dark Purplish-Red fruit which ripens approximately five days before the "Santa Rosa" (unpatented) Plum Tree and which is further distinguished from the Santa Rosa Plum Tree by bearing fruit whose flesh is firm, Amber in color, and lightly streaked with Red near the pit cavity. The Santa Rosa-Two Plum Tree is further characterized by large, deep green leaves. In addition, the tree has spur leaves which are characteristically narrower than the leaves that are produced on the shoots.

In a continual effort to upgrade the quality of his fruit, the applicant is constantly on the alert to locate any new varieties that may appear on the seedling fruit trees of any of his several farms. In his labors to produce new varieties, the applicant has germinated thousands of seedlings and has grown the resultant seedlings to maturity and carefully studied the characteristics of the progeny. The present variety of plum tree resulted from this procedure.

The plum tree of the present invention is noteworthy in ripening approximately five days before the Santa Rosa Plum Tree, i.e., June 23, in 1983, a very popular variety.

ORIGIN

The present variety of plum tree was a seedling which resulted from the germination by the applicant of numerous seeds at the inventor's ranch located at the corner of Kings Canyon Road and Fowler Avenue, Fresno, County of Fresno, State of California, in 1977. The seedling was of unknown origin inasmuch as the present variety was a chance seedling, its origin or cross is unknown, although it was known by the applicant in the sense that he knew that the seedling was germinated, was asexually reproduced, and was tested at his designated ranch. The subject variety was observed for several years prior to recognition of its desirable characteristics. The applicant asexually reproduced the subject plum tree by grafting scions thereof onto various standing plum trees located in the same orchard where the seedling had developed. This first propagation which occurred in 1980, resulted in progeny being produced that were found to possess the same distinctive characteristics as the original seedling. The grafted trees were grown on the applicant's ranch designated above.

BRIEF DESCRIPTION OF THE DRAWING

The accompanying drawing is a color photograph of a characteristic twig bearing typical leaves, a cluster of two plums showing their external coloration sufficiently mature for harvesting and shipment, three mature plums of the color when matured on the trees, a plum halved transversely of the suture plane to illustrate the flesh coloration and four stones, all of the subject variety.

DETAILED DESCRIPTION

Referring more specifically to the pomological details of this new and distinct variety of plum tree, the following has been observed under the ecological conditions prevailing at the ranch of the inventor located near Fresno, Calif. All major color code designations are by reference to the Munsell Limit Color Cascade. Common color names are also sometimes employed.

TREE

Size: Medium, depending upon pruning practices.
Vigor: Vigorous.
Figure: Upright, spreading, open, vase-formed, half-hardy.
Productivity: Very productive.
Regularity of bearing: Regular.
Trunk:
- *Thickness.*—Medium.
- *Texture of bark.*—Medium.

Branches:
- *Thickness.*—Medium.
- *Texture.*—Medium.
- *Color.*—Gray.
- *Lenticels.*—Medium in numbers and size.

LEAVES

Shoot:
- *Size.*—Medium to large.
- *Length.*—12.23±1.02 cm.
- *Width.*—4.99±0.47 cm.
- *Form.*—Oval, acuminate, pointed.
- *Thickness.*—Medium.
- *Color.*—Ventral Surface — Dark Green (MCC 21-15), Dorsal Surface — (MCC 20-14).

*Texture.*—Somewhat rugose.
*Marginal form.*—Regularly crenate.
*Petiole.*—Medium in length, 1.43±0.13 cm.; medium in thickness.
*Glands.*—Variable in number, generally 0 through 2; opposite in position; small; green; positioned on the base of the blade.
*Stipules.*—Small, linear, narrow and ephemeral.

Spur:
*Size.*—Large.
*Length.*—14.07±0.86 cm.
*Width.*—4.35±0.32 cm.
*Form.*—Narrow oval, to very slightly narrow obovate, long, long acuminate at the apex of the base, pointed.
*Thickness.*—Medium.
*Color.*—Dark Green, same color as described for the shoot leaves, indicated above.
*Texture.*—Nearly smooth.
*Marginal form.*—Regularly crenate.
*Petiole.*—Length — medium, 1.67±0.17 cm.
*Glands.*—Variable in number, 0 through 2; small in size; green; located at the base of the blade.
*Stipules.*—Completely lacking.

Flower buds: Small in size; short, plump, free, glabrous.
Flowers: Medium in size, white.
*Date of first bloom.*—Feb. 24, 1984.
*Date of full bloom.*—Mar. 4, 1984; an average bloom date as compared with other varieties.

FRUIT

Maturity when described: For commercial harvesting, usually approximately June 23.
Size: Uniform, medium to large.
*Axial diameter.*—5.34±0.19 cm.
*Diameter transverse in suture plane.*—5.86±0.21 cm.
*Diameter transverse in cheek plane.*—5.96±0.19 cm.
Form: Uniform; very slightly unsymmetrical; broadly ovate.
Suture: A shallow groove extending from the base to the apex but becoming shallower towards the apex; there is a slight depression at the pistil point.
Ventral surface: Rounded and slightly lipped throughout; lips are nearly equal.
Cavity: Flaring, and rounded; elongated in the suture plane with the suture showing on one side.
*Depth.*—0.87±0.13 cm.
*Breadth.*—2.28±0.19 cm.
*Markings.*—None visible.
Base: Truncated.
Apex: Rounded to truncated; slightly depressed.
Pistil point: Apical to slightly oblique.
Skin: Medium thickness; tough texture; slightly bitter; tenacious to flesh; no observed tendency to crack.
*Color.*—Purplish-Red (MCC 40-15 to 42-15), Ground Color — Amber (MCC 29-8).
*Bloom color.*—Medium Glue-Gray (MCC 2-3 to 2-4). Amount of Bloom — medium.

*Dots.*—Small in number, Light Brown in color, inconspicuous, except near the apical point where a few larger dots may occur.
*Down.*—Wanting.

Stem: Short and stout.
Flesh:
*Color.*—Amber (MCC 30-4), lightly streaked with Red next to the stone.
*Surface of the pit cavity.*—Darker than the streaked Red color of the flesh surrounding the pit cavity.
*Texture.*—Firm and meaty.
*Fibers.*—Few and tender.
*Ripening.*—Even.
*Flavor.*—Sub-acid, mild and delicate.
*Aroma.*—Wanting.
*Eating quality.*—Good to excellent.

Stone: Cling; adheres to the flesh over the upper half of the sides; free on the sides towards the base; fibers are short.
*Size.*—Medium.
*Length.*—2.42±0.11 cm.
*Breadth.*—2.02±0.10 cm.
*Thickness.*—1.20±0.09 cm.
*Form.*—Broadly oval, to broad, slightly obovate.
*Base.*—Straight.
*Hilum.*—Narrow and oblong.
*Apex.*—rounded with short, sharp needle-like tip.
*Sides.*—Variable, equal and unequal, curved on the left side.
*Surface.*—Base usually more or less necked, the neck having irregular ridges; ridges are positioned towards the base.
*Ventral edge.*—Thin; without wing throughout.
*Dorsal edge.*—Narrow with a shallow groove usually interrupted medianly.
*Color.*—Light Tan (MCC 30-2).
*Tendency to split.*—Slight.

Use: Market only.
Keeping quality: Good.
Resistance to insects: Medium.
Resistance to diseases: Unknown.
Shipping quality: Excellent.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, I claim:

1. A new and distinct variety of plum tree substantially as illustrated and described which is somewhat similar to the Santa Rosa Plum Tree (unpatented) with which it most closely resembles, but from which it is distinguished by bearing fruit which is large, uniform and a full dark Purple in color, which ripens approximately five days before the Santa Rosa Plum (unpatented) and has a firm, Amber-colored, lightly streaked Red flesh, and furthermore which has leaves which are a Deep Green and spur leaves which are characteristically narrower than the short leaves.

* * * * *

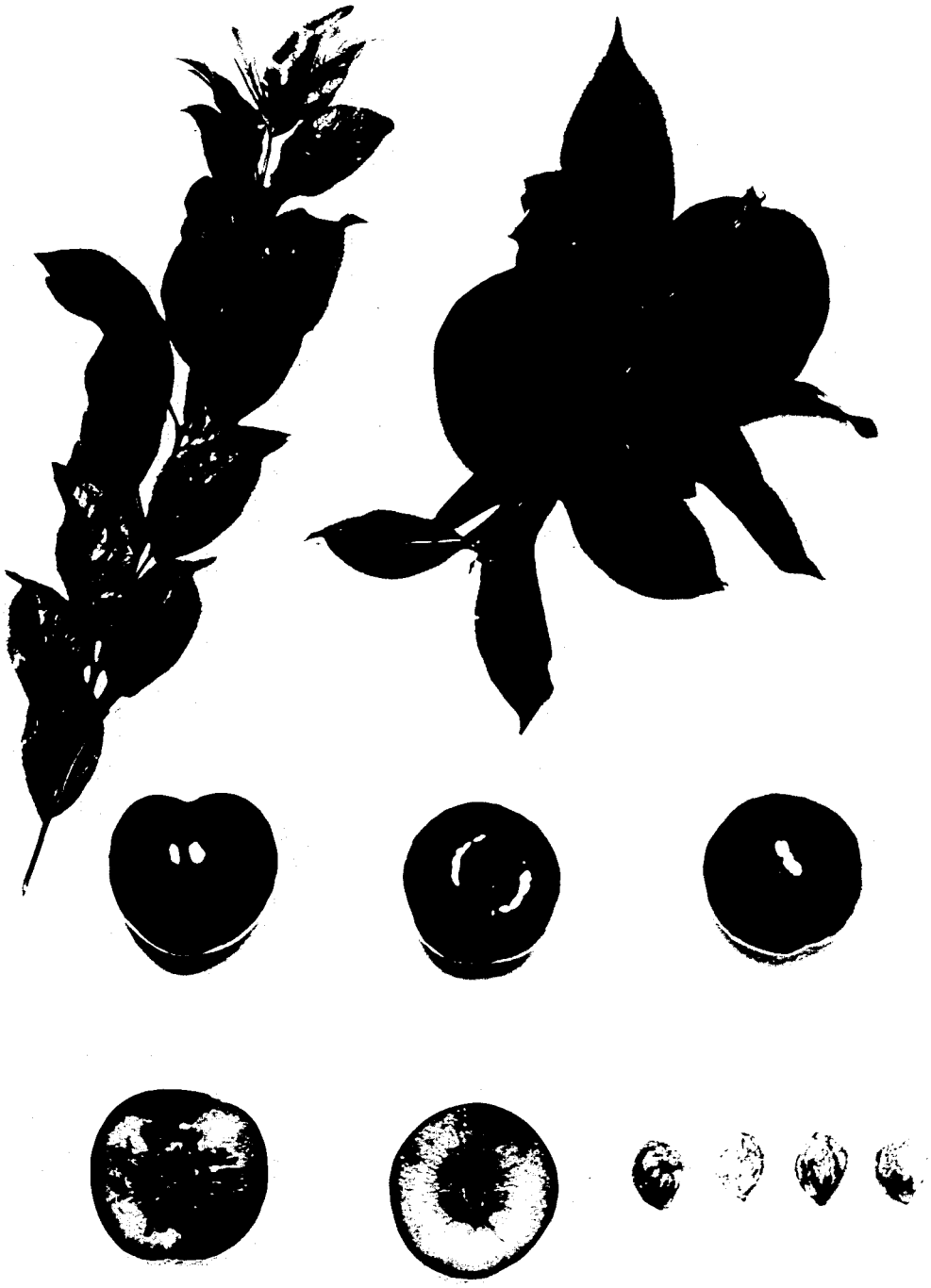

UNITED STATES PATENT AND TRADEMARK OFFICE

CERTIFICATE OF CORRECTION

PATENT NO. : PP 5,904

DATED : March 17, 1987

INVENTOR(S) : John M. Garabedian

It is certified that error appears in the above-identified patent and that said Letters Patent is hereby corrected as shown below:

Column 3, line 63, delete "Glue-Gray" and substitute ---Blue-Gray---.

Column 4, line 27, delete "rounded" and substitute ---Rounded---.

Signed and Sealed this

Thirtieth Day of June, 1987

*Attest:*

DONALD J. QUIGG

*Attesting Officer*

*Commissioner of Patents and Trademarks*